US008080490B2

(12) United States Patent
Fechner et al.

(10) Patent No.: US 8,080,490 B2
(45) Date of Patent: *Dec. 20, 2011

(54) ANTIMICROBIAL PHOSPHATE GLASS

(75) Inventors: Jörg Hinrich Fechner, Mainz (DE);
José Zimmer, Ingelheim (DE); Karine Seneschal, Mainz (DE)

(73) Assignee: Schott AG, Mainz (DE)

( * ) Notice: Subject to any disclaimer, the term of this patent is extended or adjusted under 35 U.S.C. 154(b) by 910 days.

This patent is subject to a terminal disclaimer.

(21) Appl. No.: 10/545,738

(22) PCT Filed: Feb. 20, 2004

(86) PCT No.: PCT/EP2004/001670
§ 371 (c)(1),
(2), (4) Date: Aug. 16, 2005

(87) PCT Pub. No.: WO2004/076371
PCT Pub. Date: Sep. 10, 2004

(65) Prior Publication Data
US 2006/0172877 A1  Aug. 3, 2006

(30) Foreign Application Priority Data

Feb. 25, 2003 (DE) .............................. 103 08 186
Sep. 9, 2003 (DE) .............................. 103 41 856

(51) Int. Cl.
*C03C 8/08* (2006.01)
*C03C 10/00* (2006.01)
*C03C 10/02* (2006.01)
*C03C 8/02* (2006.01)
*C03C 8/06* (2006.01)
*C03C 8/04* (2006.01)
*C03C 12/00* (2006.01)
*C03C 13/00* (2006.01)
*C03C 13/06* (2006.01)
*C03C 3/16* (2006.01)
*C03C 3/17* (2006.01)

(52) U.S. Cl. .................. 501/24; 501/2; 501/10; 501/21; 501/25; 501/26; 501/33; 501/35; 501/36; 501/45; 501/48

(58) Field of Classification Search .................. 501/48, 501/45, 2, 10, 21, 24, 25, 26, 33, 35, 36
See application file for complete search history.

(56) References Cited

U.S. PATENT DOCUMENTS

| | | | |
|---|---|---|---|
| 3,785,835 A | 1/1974 | Izumitani et al. | |
| 3,798,041 A | 3/1974 | Izumitani et al. | |
| 3,926,246 A | 12/1975 | Corbett et al. | |
| 4,092,139 A | 5/1978 | Ference | |
| 4,110,245 A * | 8/1978 | Yamashita | 501/87 |
| 4,303,298 A * | 12/1981 | Yamashita | 252/587 |
| 4,831,074 A * | 5/1989 | Moriwaki et al. | 524/494 |
| 5,022,921 A | 6/1991 | Aitken | |
| 5,034,353 A | 7/1991 | Shibuya et al. | |
| 5,074,916 A | 12/1991 | Hench et al. | |
| 5,196,381 A | 3/1993 | Hu et al. | |
| 5,212,122 A | 5/1993 | Pannhorst et al. | |
| 5,234,871 A | 8/1993 | Krashkevich | |
| 5,236,495 A * | 8/1993 | Manabe et al. | 106/35 |
| 5,290,544 A | 3/1994 | Shimono et al. | |
| 5,290,554 A | 3/1994 | Tolpa et al. | 424/195.1 |
| 5,328,874 A | 7/1994 | Beall et al. | |
| 5,544,695 A | 8/1996 | Harasym | 164/437 |
| 5,639,702 A | 6/1997 | Imashita et al. | |
| 5,807,641 A | 9/1998 | Oku et al. | |
| 5,834,008 A | 11/1998 | Greenspan et al. | |
| 6,074,984 A | 6/2000 | Demmel et al. | |
| 6,123,743 A | 9/2000 | Carman et al. | |
| 6,143,318 A | 11/2000 | Gilchrist et al. | 424/446 |
| 6,245,732 B1 | 6/2001 | Gallon et al. | |
| 6,409,396 B1 * | 6/2002 | Marker et al. | 385/88 |
| 6,593,260 B2 | 7/2003 | Nomura | 501/48 |
| 6,831,028 B1 | 12/2004 | Ishii et al. | |
| 6,846,760 B2 | 1/2005 | Siebers et al. | |
| 2001/0006987 A1 | 7/2001 | Nomura | |
| 2001/0023156 A1 | 9/2001 | Nomura | 442/123 |
| 2002/0001604 A1 | 1/2002 | Shigeru et al. | |
| 2002/0086039 A1 | 7/2002 | Lee et al. | |
| 2003/0129413 A1 | 7/2003 | Greiner et al. | 428/426 |
| 2004/0137075 A1 | 7/2004 | Fechner et al. | |
| 2004/0166172 A1 | 8/2004 | Rosati et al. | |
| 2004/0253321 A1 | 12/2004 | Fechner et al. | |
| 2005/0064193 A1 | 3/2005 | Fechner et al. | |
| 2005/0069592 A1 | 3/2005 | Fechner et al. | |

(Continued)

FOREIGN PATENT DOCUMENTS

CN  1323527  11/2001

(Continued)

OTHER PUBLICATIONS

Speier et al., "Destruction of Microorganisms by Contact with Solid Surfaces", Journal of Colloid and Interface Science, vol. 89, No. 1, pp. 68-76, Sep. 1982.
Kenaway, El-Refaie et al., "Biologically active polymers: synthesis and antimicrobial activity of modified glycidyl methacrylate polymers having a quaternary ammonium and phosphonium groups", Journal of Control Release (1998), pp. 145-152.
Gottenbos, B. et al., "Initial adhesion and surface growth of *Pseudomonas aeruginosa* on negatively and positively charge poly(methacrylates)", Journal of Materials Science: Materials in Medicine 10 (1999) 853-855.

*Primary Examiner* — David M. Brunsman
*Assistant Examiner* — Kevin Johnson
(74) *Attorney, Agent, or Firm* — Baker & Daniels LLP

(57) ABSTRACT

The invention relates to an antimicrobial phosphate glass having the following composition in percent by weight on an oxide basis: $P_2O_5$>66-80 percent by weight; $SO_3$ 0-40 percent by weight; $B_2O_3$ 0-1 percent by weight; $Al_2O_3$>6.2-10 percent by weight; $SiO_2$ 0-10 percent by weight; $Na_2O$>9-20 percent by weight; CaO 0-25 percent by weight; MgO 0-15 percent by weight; SrO 0-15 percent by weight; BaO 0-15 percent by weight; ZnO>0-25 percent by weight; $Ag_2O$ 0-5 percent by weight; CuO 0-10 percent by weight; $GeO_2$ 0-10 percent by weight; $TeO_2$ 0-15 percent by weight; $Cr_2O_3$ 0-10 percent by weight; J 0-10 percent by weight; F 0-3 percent by weight.

26 Claims, No Drawings

U.S. PATENT DOCUMENTS

| | | | |
|---|---|---|---|
| 2005/0119105 A1 | 6/2005 | Zimmer et al. |
| 2005/0176573 A1 | 8/2005 | Thoma et al. |
| 2005/0233888 A1 | 10/2005 | Seneschal et al. |
| 2006/0142413 A1 | 6/2006 | Zimmer et al. |
| 2006/0166806 A1 | 7/2006 | Fechner et al. |
| 2007/0122356 A1 | 5/2007 | Kessler et al. |

FOREIGN PATENT DOCUMENTS

| | | |
|---|---|---|
| CN | 1379146 | 11/2002 |
| DE | 2 239 307 | 2/1974 |
| DE | 2 346 778 | 3/1974 |
| DE | 28 00 145 | 9/1978 |
| DE | 39 39 831 | 6/1990 |
| DE | 302 011 | 11/1994 |
| DE | 195 03 167 | 8/1996 |
| DE | 199 60 548 | 6/2001 |
| DE | 100 17 701 | 10/2001 |
| DE | 103 09 826 | 9/2004 |
| EP | 0 141 580 | 5/1985 |
| EP | 0 220 333 | 5/1987 |
| EP | 0 425 927 | 5/1991 |
| EP | 0 648 713 | 9/1996 |
| EP | 0 921 105 | 6/1999 |
| EP | 0 773 196 | 7/2001 |
| EP | 1 116 698 | 7/2001 |
| EP | 1 116 700 | 7/2001 |
| EP | 1 270 527 | 2/2003 |
| EP | 1 449 816 | 8/2004 |
| GB | 1 294 337 | 10/1972 |
| GB | 1 316 160 | 5/1973 |
| GB | 2 178 422 | 2/1987 |
| JP | 61-133813 | 6/1986 |
| JP | 61-186248 | 8/1986 |
| JP | 3-146436 | 6/1991 |
| JP | 4-338129 | 11/1992 |
| JP | 7-25635 | 1/1995 |
| JP | 7-025635 | 1/1995 |
| JP | 7-48142 | 2/1995 |
| JP | 7-291654 | 11/1995 |
| JP | 7-300339 | 11/1995 |
| JP | 8-48539 | 2/1996 |
| JP | 8-175843 | 7/1996 |
| JP | 8-217492 | 8/1996 |
| JP | 8-245240 | 9/1996 |
| JP | 10-059788 | 3/1998 |
| JP | 10-101364 | 4/1998 |
| JP | 10-158037 | 6/1998 |
| JP | 10-218637 | 8/1998 |
| JP | 10-231187 | 9/1998 |
| JP | 11-29343 | 2/1999 |
| JP | 11-060277 | 3/1999 |
| JP | 11-209143 | 8/1999 |
| JP | 11-228173 | 8/1999 |
| JP | 11-278866 | 10/1999 |
| JP | 11-319042 | 11/1999 |
| JP | 2000-053451 | 2/2000 |
| JP | 2000-191339 | 7/2000 |
| JP | 2000-203876 | 7/2000 |
| JP | 2000-264674 | 9/2000 |
| JP | 2000-327369 | 11/2000 |
| JP | 2001-026466 | 1/2001 |
| JP | 2001-048595 | 2/2001 |
| JP | 2001-247333 | 9/2001 |
| JP | 2001-247334 | 9/2001 |
| JP | 2001-247335 | 9/2001 |
| JP | 2001-247336 | 9/2001 |
| JP | 2002-12442 | 1/2002 |
| JP | 2003-206139 | 7/2003 |
| JP | 2001-247337 | 10/2008 |
| WO | 96/21628 | 7/1996 |
| WO | 97/27148 | 7/1997 |
| WO | WO 98/44965 | 10/1998 |
| WO | 00/15167 | 3/2000 |
| WO | 00/38552 | 7/2000 |
| WO | WO 00/49996 | 8/2000 |
| WO | 00/66086 | 11/2000 |
| WO | 00/76486 | 12/2000 |
| WO | WO 01/03650 | 1/2001 |
| WO | 01/72262 | 10/2001 |
| WO | WO 0172262 | * 10/2001 |
| WO | 02/28792 | 4/2002 |
| WO | 03/018495 | 3/2003 |
| WO | WO 03/018496 | 3/2003 |
| WO | WO 03/018498 | 3/2003 |
| WO | WO 03/018499 | 3/2003 |
| WO | 03/062163 | 7/2003 |
| WO | WO 2004/076369 | 9/2004 |
| WO | WO 2004/076370 | 9/2004 |
| WO | WO 2004/076371 | 9/2004 |

* cited by examiner

ANTIMICROBIAL PHOSPHATE GLASS

The invention relates to antimicrobial phosphate glasses, glass ceramics and ceramics obtained from said antimicrobial phosphate glasses as well as glass powder and glass ceramic powder based on phosphate glasses which exhibit an antimicrobial effect. In the present application the term glass powder should also include glass fibers, glass pellets, and glass beads.

U.S. Pat. No. 5,290,554 describes water soluble glasses for application in cosmetic products with very low $SiO_2$ contents and very high $B_2O_3$ contents or high $P_2O_5$ contents. The glasses exhibit silver concentrations<0.5 percent by weight. These glasses possess an extremely low hydrolytic resistance and have the disadvantage of completely dissolving in water. The anti-bacterial effect in these glasses is caused by the nascent Ag and/or Cu ions.

U.S. Pat. No. 6,143,318 describes silver-content phosphate glasses which use combinations of Cu Ag and Zn as antimicrobial material for treatment of infected wounds. The disadvantage of these glasses was the low hydrolytic resistance, which is revealed in the fact that the glasses were completely water-soluble. This glass does not contain any $Al_2O_3$, which is necessary for setting of the hydrolytic resistance. Further, the concentration of $Na_2O$ with 34 mol % is quite high. This causes the reactivity of the glass to be quite high and it completely dissolves relatively quickly.

Phosphate and/or borophosphate glasses are well-known from the following publications
JP-A 2001-247333 and JP-A 2001-247336
JP-A 2001-247335
JP-A 8175843.

These systems have the disadvantage of being highly reactive in combination with too low a chemical resistance.

JP-A 2001-247333 describes a glass fiber which in a later processing step is anti-microbially finished with $Ag_2O$. The glass compositions known from JP-A 2001-247333 have a low $Na_2O$ content. Higher alkali contents are obtained in JP-A 2001-247333 or the corresponding US 2001/0023156 through the use of $K_2O$ and/or $Li_2O$. However, this has the disadvantage that mixed alkali effects can occur in the glass composition. This results in non-linear reactivity changes. Consequently the reactivity can no longer be precisely set.

JP-A 2001-247336 and JP-A 2001-247335 also describe a glass composition which is antimicrobially finished with $Ag_2O$ in a subsequent processing step. The glasses known from JP-A 2001-247336 or from the corresponding US 2001/0006987 as well as from JP-A 2001-247335 are borophosphate glasses with $B_2O_3$ content. Moreover JP-A 2001-247335 stands out due to a relatively low phosphoric content in the glass.

JP-A 8175843 describes a glass containing very high ZnO concentrations (35-45 mol % ZnO). These high ZnO concentrations have a negative effect on the chemical resistance of the glasses. The glass possesses only an inadequate long-term stability.

In the case of all of the glass compositions in which a subsequent addition of $Ag_2O$ is present, composite materials are formed in which silver or silver agglomerates are accumulated on the surface of the vitreous phase, so that no homogeneous distribution of the silver is present.

In JP 92338129 a soluble glass is described which achieves its antimicrobial effect solely by means of the addition of silver. The glass in accordance with JP 92338129 is moreover free from Zn. This is disadvantageous, since zinc contributes synergistically to the desired antimicrobial effect.

An initial object of the invention is to specify a glass composition which avoids the drawbacks of the state of the art, exhibits an antimicrobial effect, a high chemical resistance as well as a high reactivity.

This object can be solved by a glass or glass ceramic powder comprising the following composition in percent by weight on an oxide basis:

| | | |
|---|---|---|
| $P_2O_5$ | >66-80 | percent by weight |
| $SO_3$ | 0-16.8 | percent by weight |
| $B_2O_3$ | 0-1 | percent by weight |
| $Al_2O_3$ | >6.2-10 | percent by weight |
| $SiO_2$ | 0-10 | percent by weight |
| $Na_2O$ | >11-20 | percent by weight |
| $Li_2O$ | 0 | percent by weight |
| $K_2O$ | 0 | percent by weight |
| CaO | 0-16.8 | percent by weight |
| MgO | 0-15 | percent by weight |
| SrO | 0-15 | percent by weight |
| BaO | 0-15 | percent by weight |
| ZnO | >0-16.8 | percent by weight |
| $Ag_2O$ | 0-5 | percent by weight |
| CuO | 0-10 | percent by weight |
| $GeO_2$ | 0-10 | percent by weight |
| $TeO_2$ | 0-15 | percent by weight |
| $Cr_2O_3$ | 0-10 | percent by weight |
| I | 0-10 | percent by weight |
| F | 0-3 | percent by weight. |

The antimicrobial phosphate glasses of the invention stand out by means of an increased $Na_2O$ content in comparison with the glasses of the state of the art. As a result of this an improved reactivity combined with a more uniform release of the biocide ions is achieved and with it a higher antimicrobial effect compared to the state of the art, since in these glasses the antimicrobial ions such as Ag or Zn can be released particularly well. A further advantage of such glasses is that contents of $Na_2O$>9% reduce the Tg of the glass. Tg is understood to be the transformation temperature of the glass, as described for example in the VDI-Lexikon Werkstoff-Technik (1993), pages 375-376. This makes it possible for the glass to be melted at lower temperatures.

In addition, through the $Na_2O$ the thermal expansion coefficient a is increased, so that a better temperature stability is given with the polymer.

In the case of glass polymer composites at least a partial melting in high temperature polymers such as e.g. PEEK is possible. Also the use of other alkalis besides Na alone is possible, for example K or Li.

A second object of the invention is to specify a glass composition that is free of alkali, but which nevertheless exhibits a sufficient antimicrobial effect as well as a high chemical resistance.

By antimicrobial effectiveness a biocide or biostatic effect is understood including bacteria, fungi, algae, yeasts etc.

This task is achieved by means of a glass composition that is to a large extent free of alkali, a glass ceramic or a glass powder or glass ceramic powder in accordance with the invention.

The composition in accordance with the second aspect of the invention additionally stands out due to the fact that it is to a large extent free of tin, that is free of Sn with the exception of impurities. Since Sn in glass supports the reduction of ionic Ag+ to metallic silver, glasses containing Sn discolor in an undesirable manner.

In addition a plastic glass or glass ceramic composite in accordance with the invention.

With the inventive glass composition, in case $Ag_2O$ is introduced, in contrast to the state of the art $Ag_2O$ is homogeneously distributed in the glass.

In case no silver is present in the glass composition with the exception of impurities, i.e. $Ag_2O$=0 percent by weight, preferably the glass contains more than 5 percent by weight ZnO for the purpose of achieving the antimicrobial effect.

This is in particular preferred when silver is added to the glass in a form that does not act in an oxidizing manner e.g. as silver nitrate and is not melted under oxidizing conditions and a discoloration of the glass is to be prevented, because e.g. there can be a discoloration with such argentiferous glasses in the case of exposure to light or by means of oxidation-reduction processes in the glass.

The addition of silver quite often leads to changes in the glass. Such a discoloration can be avoided when silver is added to the glass in the batch in a form that has an oxidizing effect, e.g. as silver nitrate ($AgNO_3$). Further the glass is preferably melted under oxidizing conditions, e.g. by means of oxygen bubbling, in order to achieve an oxidizing state in the glass and consequently avoid a reduction of the $Ag^+$ to metallic $Ag^0$. This can also be achieved by means of tank setting such as e.g. by means of oxidative port settings. Other components such as e.g. alkalis, alkaline earths can also be added preferably as oxidative acting components, such as e.g. nitrate, peroxide.

Other components such as alkalis, alkaline earths can also be preferably added to the raw material batch as nitrate.

The total content in nitrates amounts preferably to more than 0.5 or 1 percent by weight, especially preferably to more than 2.0 percent by weight, while more than 3.0 percent by weight is most especially preferable.

A silver concentration of 1 percent by weight is especially preferable when a strong antimicrobial effectiveness with simultaneously lower or no discoloration is required and oxidative additives such as e.g. nitrates cannot be added to the batch during melting.

In an advanced embodiment with glass compositions with a low alkali content the glass composition is free of aluminum as well as free of heavy metals except for zinc. By adding zinc the antimicrobial effect is strengthened in such glass compositions.

The glass composition or glass ceramics obtained from it or glass powders or glass ceramic powders obtained from it are toxicologically generally recognized as safe for use in cosmetics/medicine and are free from heavy metals except for Zn.

With regard to use in those areas in which the glass comes into direct contact with human beings, in particular skin tissue or body fluids, compositions that are free from alkalis and free from aluminum are particularly well suited.

The glass compositions or the glass ceramics obtained from them can be used for the purpose of preservation of the products themselves as well as for achieving an antimicrobial effect outwards, i.e. a release of antimicrobial acting substances, in particular ions such as e.g. zinc or silver.

The toxicological quality of being generally recognized as safe is not a condition for the use of glass compositions or glass ceramics or glass powders or glass ceramic powders in order to make available an antimicrobial/biocide effect in products such as paints and enamels. In this case the composition can contain $Cr_2O_3$ or CuO.

The inventive glass compositions or glass ceramics or glass powders or glass ceramic powders can be used for preservation of the products themselves and/or for the achievement of an antimicrobial effect outwards, i.e. of a release of antimicrobial acting substances, in particular ions such as e.g. zinc or silver.

The glass or glass ceramic or the glass powder or glass ceramic powder can in the case of sufficient high hydrolytic resistance also be applied to a polymer as a coating, i.e. protective coating.

If the glass compositions or glass ceramics or glass powders or glass ceramic powders are used for example in paints and enamels in order to make available an antimicrobial/biocide effect in products, the toxicological quality of being generally recognized as safe is not a condition and the composition can contain $Cr_2O_3$ or CuO.

In application in specific plastics or enamels and under certain conditions alkali free compositions have the advantage that the polymer chain is not broken up and consequently the polymer material is not locally destroyed.

This ensures that there is no lasting damage to the mechanical and optical properties of the polymer material.

In particular the polymer chains, e.g. in polycarbonates, are not attacked, so that the mechanical and optical properties of polycarbonates are not negatively influenced by the inventive glass powder as an aggregate.

In comparison to the silicate glasses known from the state of the art, the phosphate glasses described here possess a higher reactivity and consequently a better antimicrobial effectiveness. In addition, the phosphate glasses described here have a low Tg and can consequently be processed at a lower temperature, hence facilitating the processing.

Furthermore, in the case of mixtures of the relatively low-melting glasses described here with refractory polymers there can be a partial or complete fusing of the glasses so that the glasses form a more intimate bond to the polymer, which can lead to an extremely homogenous distribution in the polymer. A fusing of the glasses as described can for example in the processing of inventive polymer glass composite materials result in plastic semi-finished materials or plastic products with biocide properties. In this regard particular reference is made to fusing in the case of extruding of the polymer-glass composite materials. By means of this fusing the antimicrobial effectiveness is increased as well as a higher strength of the polymer-glass composite materials is achieved. In addition the combustibility or temperature resistance of the material is increased. In the case of the silicate glasses known from the state of the art, for example from PCT/EP03/00559, which plastics can be admixed to, such a fusing is not observed. What is more the antimicrobial effect of such mixtures is significantly lower than in the case of mixtures of plastics with the inventive glasses.

The glass composition of the invention also exhibits anti-inflammatory and wound healing properties. This is in particular of advantage for use in the field of cosmetics, medicine.

The alkaline glass composition comprises the following components, in percent by weight on an oxide basis:

| | | |
|---|---|---|
| $P_2O_5$ | >66-80 | percent by weight |
| $SO_3$ | 0-40 | percent by weight |
| $B_2O_3$ | 0-1 | percent by weight |
| $Al_2O_3$ | >6.2-10 | percent by weight |
| $SiO_2$ | 0-10 | percent by weight |
| $Na_2O$ | >9-20 | percent by weight |
| $K_2O$ | 0-25 | percent by weight |
| CaO | 0-25 | percent by weight |
| MgO | 0-15 | percent by weight |
| SrO | 0-15 | percent by weight |

-continued

| | | |
|---|---|---|
| BaO | 0-15 | percent by weight |
| ZnO | >0-25 | percent by weight |
| Ag$_2$O | 0-5 | percent by weight |
| CuO | 0-10 | percent by weight |
| GeO$_2$ | 0-10 | percent by weight |
| TeO$_2$ | 0-15 | percent by weight |
| Cr$_2$O$_3$ | 0-10 | percent by weight |
| I | 0-10 | percent by weight |
| F | 0-3 | percent by weight |

The Na$_2$O content preferably amounts to >9.5 percent by weight, especially preferably >10 percent by weight while 10.5 percent by weight is most especially preferable. A most preferably embodiment contains >11 percent by weight or 11.5 percent by weight Na$_2$O.

Those alkaline glass compositions are preferable upon the presence of Na with the exception of impurities free of Li and K.

In a second embodiment of the invention the alkali free glass composition comprises the following components in percent by weight on an oxide basis:

| | | |
|---|---|---|
| P$_2$O$_5$ | >66-80 | percent by weight |
| SO$_3$ | 0-40 | percent by weight |
| B$_2$O$_3$ | 0-1 | percent by weight |
| Al$_2$O$_3$ | 0-3.9 | percent by weight |
| SiO$_2$ | 0-10 | percent by weight |
| CaO | 0-25 | percent by weight |
| MgO | 0-15 | percent by weight |
| SrO | 0-15 | percent by weight |
| BaO | 0-15 | percent by weight |
| ZnO | 1-25 | percent by weight |
| Ag$_2$O | 0-5 | percent by weight |
| CuO | 0-10 | percent by weight |
| GeO$_2$ | 0-10 | percent by weight |
| TeO$_2$ | 0-15 | percent by weight |
| Cr$_2$O$_3$ | 0-10 | percent by weight |
| I | 0-10 | percent by weight |
| F | 0-3 | percent by weight | whereby the sum of the alkali contents is less than 0.4 percent by weight, preferably less than 0.1 percent by weight most preferably less than 0.01 percent by weight and the composition is to a large extent free of Sn with the exception of impurities.

In the case of the inventive glasses or glass ceramics or glass powders which are obtained proceeding from the above named glass composition, surprisingly in the specified composition range a sufficient chemical resistance, a high reactivity and a skin-neutral to pH-neutral value are identified. The glass, in particular however, the glass powder, exhibits either a biocidal effect, or at least a biostatic effect. On the basis of the skin-neutral to pH-neutral value in the aqueous solution, the glass or the glass powder obtained from it or the glass ceramic obtained from it or the glass ceramic powder obtained from it is skin compatible in contact with human beings. In addition the glass is toxicologically generally recognized as safe. The load of the heavy metals is preferably less than 20 ppm for Pb, less than 5 ppm for Cd, less than 5 ppm for As, less than 10 ppm for Sb, less than 1 ppm for Hg, less than 10 ppm for Ni. Upon contact with water there is an exchange of ions in the case of the inventive glass, for example an exchange of Na ions or of Ca ions between the glass surface and the flowing medium. The reaction rate or rate of dissolution can be set by means of variation of the glass forming P$_2$O$_5$ component, that is, the network-forming P$_2$O$_5$ component. The release rate of biocidal ions is set by means of the exchange of ions and the dissolution of the glass. In order to obtain the chemical resistance in fulfillment of the requirements, i.e. to obtain a hydrolytic resistance that is not too low, the alkaline glass contains preferably Al$_2$O$_3$ in concentrations >6 percent by weight. Preferably the ratio between Na/Al lies between 2:1-1:1 percent by weight. Na and Al contribute to the structure of the glass network in a molar ratio of 1:1. Excess Na then acts as a network modifier. Hence the reactivity of the glass can be set directly via the Na/Al ratio.

By means of the purposeful introduction of Na$_2$O, as well as CaO in the case of alkaline compositions the network formation is interrupted and the reactivity of the glass is set, since in the case of high Na$_2$O content the network is looser and introduced biocidal acting ions such as Zn, Ag can be more easily transferred. Na$_2$O contents of >10 percent by weight have proven to be especially preferable in case the glass matrix contains solely Na$_2$O and Na$_{20}$>5 percent by weight as well as CaO>5 percent by weight in the case of Na$_2$O and CaO being introduced.

In the case of alkali free glass compositions the network formation can be interrupted and the reactivity of the glass can be set by means of the purposeful introduction of network-modifying alkaline earth ions, since in the case of high alkaline earth contents the network is looser and introduced biocidal acting ions such as Zn can be more easily transferred.

The pH value can be set to a skin-neutral value by means of the ion exchange of the Na ions or Ca ions in an aqueous solution as well as the OH groups of the phosphorous oxides which do not contribute to the structure of the glass network. The percentage of the OH groups of the phosphorous oxides not contributing to the structure of the glass network can be defined by means of the batch composition for one, for another can be influenced by means of melting parameters such as melting period, purity of the raw materials etc.

By means of the purposeful setting of the Na$_2$O content with non-alkali free glass compositions as well as of the CaO content in ratio to the P$_2$O$_5$ content or the OH groups of the phosphorous oxide not contributing to the structure of the glass network it is possible to precisely set the pH value of the glass in contact with water by means of variation of the glass composition or by means of variation of the melting parameters. A setting is achieved over a wide pH value range of 4.0 to 7.0.

In the case of alkali free glass compositions the pH value of the glass in contact with water can be precisely set by means of the purposeful setting of the CaO content in ratio to the P$_2$O$_5$ content or the OH groups of the phosphorous oxide not contributing to the structure of the glass network by means of variation of the glass composition or by means of variation of the melting parameters. A setting over a wide pH range of 4.0 to 8.5 is achieved, with 4.5 to 7 being especially preferable.

Glasses which exhibit an amount of CaO>5 percent by weight are especially preferable, because the Ca has a special function. In the presence of Ca the glass can become bioactive. The bioactivity is characterized by the fact among other things a mineral layer develops on the particle surface, the so-called hydroxylapatite layer. This layer is quite similar to the hard tissue of the human organism and for this reason is quite compatible both with hard tissue as well as with soft tissue.

If a glass composition is present in which an antimicrobial effect of the glass is caused by means of ions such as zinc or even slight silver content, this antimicrobial effect is additionally supported in the case of alkaline glasses by released alkaline ions, such as Na, K or alkaline earths; in the case of alkali free glasses by the alkaline earth ions, such as Ca or Ba.

The antimicrobial effect occurs because the osmotic balance of the cells is disturbed. In a most especially preferred embodiment the glass composition contains Ca and Zn in ratios of 1:1 to 1:2 in percent by weight. For example this is achieved by an embodiment which contains 8 percent by weight CaO and 8.5 percent by weight ZnO.

This preferred embodiment with Ca and Zn in ratio of 1:1 to 1:2 stands out due to the fact that for one thing it possesses the antimicrobial effect and on the other hand it is also particularly "biocompatible", i.e. it is particularly compatible in contact with the body tissue.

The embodiments of the invention which stand out due to their toxicological quality of being generally recognized as safe are particularly suitable for use in creams or lotions or similar offerings in order to apply them to the skin.

Possible applications in the field of medicine are the reduction or prevention of skin irritations such as erythema, irritation, as well as caring for wounds in the cosmetic and medical fields.

Another field of application is food preservation.

For applications in fields in which the glass, the glass ceramic or glass powder or glass ceramic powder obtained from the glass comes into contact with human beings, for example in applications in the field of medicine, cosmetics etc. the glass is preferably free from other heavy metals. Pure raw materials are also used preferably with such applications.

The biocide or biostatic effect of the inventive glass or glass powder obtained from it or of the inventive glass ceramics obtained from these source glasses is brought about by means of releasing ions in a fluid medium, in particular in water. The glasses or the glass powders and glass ceramics obtained from them exhibit a biocidal effect toward bacteria, fungi as well as viruses. This effect is brought about in particular by the presence of zinc.

For applications in fields in which there is no direct contact with human beings the inventive glasses or glass powders or glass ceramics can also exhibit heavy metal ions for the achievement of a particularly strong biocidal effect. Such heavy metal ions are Ag, Cu, Ge, Te and Cr. Glasses or glass powders or glass ceramics in accordance with the invention can be added to polymers, paints and lacquers.

One preferred application field of the glasses or the glass ceramics, glass powders or glass ceramic powders obtained from the glasses in accordance with the invention is the use in polymers for the achievement of a biocidal or biostatic effect. For one thing a preservation of the polymer itself can be in the foreground, i.e. protecting the polymer from bacteria and fungal attack. In addition a biostatic or biocidal polymer surface can be created herewith, whereby if possible no biocidal active substances e.g. ions are to be transferred to the environment.

An additional objective can be the provision of a polymer which in particular releases biocidally active substances.

In an additional aspect of the invention for this reason a plastic-glass composite is made available whereby the plastic-glass composite material includes:
 a plastic material
 a glass and/or a glass ceramic
  based on one of the afore-mentioned alkaline or alkali free glass compositions Surprisingly it turns out that in a preferred embodiment of the invention a strong antimicrobial effect when using alkali free glasses is also achieved without the presence of alkalis in the glass matrix. Usually the reactivity of the glass is set via the alkali ion content and hence the strength of the antimicrobial effect is set both chronologically and quantitatively. In the alkali free glasses described here a variable reactivity can also be set without alkali ions. In the case of the inventive alkali free glasses the alkaline earths of the glass are replaced by $H^+$-ions of the aqueous medium by means of reactions on the surface of the glass. By adding antimicrobial acting ions such as Zn the antimicrobial effect of the glass composition can be further strengthened. With the inventive glass composition or glass ceramic composition it is consequently possible to set even the antimicrobial effect by means of variation of the alkaline earth content as well as by means of the antimicrobial active zinc.

In the use of both alkali free and alkaline glass compositions or glass ceramics or glass powders or glass ceramic powders from such glass compositions in polymers it is expected that due to the shielding of aqueous media they are only insufficiently antimicrobial, because they are encapsulated by polymers. Surprisingly it turns out that even by the addition of very slight quantities of Ag and/or other biocidal ions such as Zn, Cr, Cu, a significant antimicrobial effect of the glass, the glass ceramic, of the glass powder or of the glass ceramic powder occurs in a polymer matrix.

This is surprising because a very slight water content in conventionally manufactured polymer is already sufficient to "activate" the silver ions and/or other biocidal ions in the glass matrix, and hence achieve an antimicrobial long-term effect.

If the polymer-glass-composite containing such glass compositions, glass ceramics, glass powders or glass-ceramic powders is heated up, the glass can partially melt depending on the set processing temperature, as a result of which the antimicrobial effect is increased. Other properties of the composite material such as the strength are also positively influenced.

A further developed embodiment of the invention provides for the glass composition to also comprise Ca and Zn and has the sum of CaO and ZnO in the range of 5-40 percent by weight in this glass composition. Preferably the ZnO content in this sum is more than 0.1 percent by weight, preferably more than 1 percent by weight.

As stated earlier, the glasses with the inventive compositions or glass ceramics, glass powders or glass ceramic powders obtained from said compositions evince a biostatic or biocidal effect in polymers. This can be used to preserve polymers, in particular protecting them from fungal attack or decomposition by bacteria. It is also conceivable to equip a polymer with an antimicrobial surface. Such an antimicrobial surface if at all possible should not release or transfer any antimicrobial active substances, in particular ions, outward, i.e. outside of the polymer surface.

The inventive glasses, in particular the alkali-free glasses, also make possible a slow release of antimicrobial active ions from a polymer matrix.

In the process the water content of the polymer as well as the diffusion of the mobile ions in the polymer matrix play a deciding role. In general the biocidal ion content in the glass matrix or the concentration of glass in the polymer is higher than in the afore-mentioned application. This release can be combined with a partial or complete melting of the glass. In a particularly preferred embodiment the polymer matrix dissolves either partially or completely. This is in particular the case when the polymer matrix is water-soluble.

A further developed embodiment of the invention provides that the glass, the glass ceramic obtained from it as well as the glass powder or glass ceramic powder obtained from the glass in the case of sufficient hydrolytic stability is not contained in the polymer itself, but rather can also be applied to the polymer as a protective coating or coating.

To ensure a compatibility with the polymer and to set the reactivity the amount of CaO is preferably more than 1 percent by weight, preferably more than 7.7 percent by weight. One further advantage of a CaO content greater than 1 percent by weight lies in the increase of the temperature load capacity of the glass.

Further fields of application of the glasses described here are use in paints and lacquers. The objective is preservation of the paints and/or achievement of a biocidal/biostatic layer or a biocidal effect outward, e.g. when a surface has mildewed.

Due to the high phosphoric content the inventive glasses, glass powders, glass ceramics or glass ceramic powders can, along with the biocidal effect, also exhibit a bioactive effect by means of exchange or release of ions. The inventive glasses, glass ceramics, glass powders or glass ceramic powders are therefore particularly biocompatible, i.e. particularly compatible with body tissue.

In a preferred embodiment the heavy metal content can be reduced by means of partial or complete replacement of Zn preferably with Ca, but also with Mg. Such substances ensure a good environmental compatibility.

In the case of the inventive glasses, glass ceramics, glass powders or glass ceramic powders ions are exchanged or released by means of reactions at the glass surface or partial melting of the glass. The antimicrobial effect is consequently based among other things on a release of ions. The antimicrobial effect caused by the exchange or release of ions impairs the cell growth.

Along with the transfer the antimicrobial glass surface introduced into the system also plays a role. The antimicrobial effect of the glass surfaces is also based on the presence of antimicrobial acting ions. Additionally however it is also known that surface charges, i.e. the zeta potential of powders can have an antimicrobial effect in particular on Gram-negative bacteria. Thus an antimicrobial effect proceeds from positive surface charges to Gram-negative bacteria, since positive surface charges attract bacteria, but Gram-negative bacteria do not grow on surfaces with positive zeta potential, i.e. cannot multiply. In this regard reference is made to Bart Gottenbos et al. Materials in Medicine 10 (1999) pages 853-855 Surface of Polymers.

Antimicrobial effects in powders with positive surface charge are described in Speier et al. Journal of Colloid and Interface Science 89 68-76 (1982) Kenway et al. Journal of controlled release 50, 145-52 (1998). By means of variation of the glass-forming, that is, the network-forming $P_2O_5$ component the rate of dissolution of the glass can be set. By means of ion exchange and melting of the glass the release rate of biocidal ions is set.

In particular the pH value can be set by means of releasing phosphates in aqueous solution, in particular by setting it to a skin-neutral value.

By means of purposeful introduction of $Na_2O$ such as ZnO or CaO with alkaline glasses the network formation is interrupted and the reactivity of the glass is set, because in the case of high $Na_2O$ content the network is looser and introduced biocidal acting ions like Zn, Ag can be more easily transferred. In the case of alkali-free glasses the reactivity is controlled by the purposeful introduction of CaO or ZnO. By means of the purposeful introduction of alkaline earth ions such as e.g. CaO or ZnO the network formation is interrupted and the reactivity of the glass is set, since in the case of high CaO content the network is looser and introduced biocidal acting ions like Zn, Ag can be more easily transferred. Inventive glasses including CaO are particularly preferable, in particular with a greater weight percentage than 5 percent by weight, because the glass becomes bioactive in the presence of Ca. Especially preferred embodiments contain Ca and Zn in the ratio of 1:1 to 1:2 percent by weight.

By means of the exchange of Na ions or Ca ions in aqueous solution the pH value can be set to a neutral value, for example pH 7. If the $P_2O_5$ content is increased or if the network of the glass is varied by means of melting parameters such as the melting period, purity of the raw materials etc., e.g. by varying the amount of free OH groups of the phosphorous oxide, then a shift into slightly acid condition can also be achieved, so that a skin-neutral pH value of pH=5.5 results.

By means of the purposeful setting of the $Na_2O$ content as well as of the CaO content in ratio to the content of the network forming component $P_2O_5$ it is possible to precisely set the pH value of the glass in contact with water by means of variation of the glass composition. A setting is achieved via a broad pH value range of 4 to 8.

The biocidal or biostatic effect of the inventive glass or glass powder obtained from said inventive glass or the inventive glass ceramics or glass ceramic powders obtained from these original glasses is caused by the release of ions in a fluid medium, in particular in water. The glasses or the glass powders and glass ceramics obtained from said glasses exhibit a biocidal effect toward bacteria, fungi as well as viruses.

Glass ceramics or ceramics can be obtained from the glasses described here. These are manufactured by means of a subsequent annealing step either on the half-finished product (e.g. the glass bands or ribbons) or on the product, for example on the glass powder or the glass powders. After the annealing step a renewed grinding may be necessary in order to set the desired particle size.

With the help of grinding processes the glass compositions can be ground up to glass powder with particle sizes<100 μm. Particles sizes<50 μm or <20 μm have proved to be practical. Particles sizes<10 μm as well as smaller than 5 μm are particularly suitable. Particle sizes<2 μm have proven to be most particularly suitable. The grinding process can be conducted either dry or using non-aqueous or aqueous grinding media.

Mixtures of different glass powders from the composition range with different compositions and particle sizes in order to combine specific effects.

Depending on the particle size, concentration and the composition of the powder pH values ranging from 4.0 to 8.0 are achieved.

Mixtures of glass powders with different compositions and particle sizes can be synergistically combined to set special properties of the individual glass powders. For example it is possible to control the antimicrobial effect of the glass powder by means of the particle size.

The glass of the glass powder contains $P_2O_5$ as a network forming ion, whereby the degree of cross-linking can be influenced among other things by melting parameters.

$Na_2O$ is used in alkaline glasses as a fluxing agent in the melting of the glass. In concentrations less than 5 percent by weight the melting behavior is negatively influenced. Moreover the necessary mechanism of the ion exchange is no longer sufficient in order to achieve an antimicrobial effect. In the case of $Na_2O$ concentrations higher than 30 percent by weight the chemical resistance is too low or the reactivity is too high. Further the melting behavior is negatively influenced.

In the case of alkaline glasses alkali oxides and alkaline earth oxides are necessary for the structure of the glass network. The desired reactivity of the glass can be set for these glasses by means of the alkali oxide and alkaline earth oxide content in the glass composition.

In the case of alkali-free glasses alkaline earth oxides are necessary for the structure of the glass network. The desired reactivity of the glass can be set by means of the alkaline earth oxide content in the glass composition.

Inventive glasses comprising CaO are particularly preferred, in particular with a weight percentage greater than 5 percent by weight, because in the presence of Ca the glass is particularly compatible to body tissue.

The amount of $Al_2O_3$ serves the purpose of increasing the chemical resistance of the crystallization stability as well as controlling the antimicrobial effect. In addition it partially contributes to the structure of the glass network. In a preferred embodiment $Al_2O_3$ is added to an alkaline glass composition at more than 6.2 percent by weight. In the case of alkaline glasses with $Al_2O_3$ contents <6.2 percent by weight the reactivity is too high, i.e. the glass reacts too quickly, in this way a long-term effect in the release of antimicrobial ions is not achieved.

With the alkali-free glasses the reactivity of the alkali-free glass is increased by means of a very low $Al_2O_3$ content <3.9 percent by weight, so that surprisingly a long-term effect is achieved in the release of antimicrobial ions. Consequently a long-term effect in the release of antimicrobial ions can be achieved both in alkaline as well as alkali-free glasses by means of the $Al_2O_3$ content.

ZnO is a significant component for the heat molding properties of the glass. It improves the crystallization stability and increases the surface tension.

ZnO possesses antimicrobial properties and is used in a preferred embodiment of the invention to achieve an antimicrobial effect, to be precise preferably in a composition which except for zinc is free from other heavy metals.

Moreover it can support the anti-inflammatory and wound healing effects. Up to 20 percent by weight of ZnO can be included for the achievement of an anti-inflammatory and wound healing effect. A preferred embodiment contains >10 percent by weight ZnO or 12 percent by weight ZnO. For purely antimicrobially acting glasses the glass matrix can also be composed without zinc.

In place of Zn the glass then preferably includes Ca. In this case an antimicrobial effect is achieved by means of biocidal active ions such as Ag, Te, Ge, Cr, Cu, which are integrated in the glass matrix. Suitable substances for this purpose are $Ag_2O$ or CuO.

Along with direct integration into the glass matrix during the melting process these ions can also be introduced only in the surface regions of the glass via an exchange of ions.

To strengthen the antimicrobial effect of the base glass $Ag_2O$, CuO can be added as antimicrobial acting additives.

The inventive glass does not bring about any skin-irritating effects.

By means of a combination of the pH effect, the effect through surface effects and the Ag, Cu or Zn transfer a considerable increase of the antimicrobial effect can be achieved, which significantly exceeds the sum of the individual effects. The concentration of Ag, Cu, Zn ions released in the product can lie significantly below 1 ppm.

The introduction of Ag, Cu, Zn can either take place during the melting by means of appropriate salts or by means of ion exchange of the glass after the melting.

For the achievement of color effects for example with applications in paints and lacquers single or even multiple color-giving components such as e.g. $Fe_2O_3$, CoO, CuO, $V_2O_5$, $Cr_2O_5$ in a total concentration less than 4 percent by weight, preferably less than 1 percent by weight can be added to the glasses Glasses, glass powders, glass ceramics or glass ceramic powders with a composition lying within the claimed composition range fulfill all requirements with regard to use in the areas of paper hygiene, cosmetics, paints, lacquers, plasters, medical products, cosmetic applications, food additives as well as use in deodorant products, antiperspirants as well as in products for the treatment of skin irritations, acute and chronic wounds as well as in the field of dental care/dental hygiene and oral care/oral hygiene as well as dental material, for example for fillings, crowns, inlets etc.

The glass powder can be used in any suitable form. Mixtures of different glass powders from the composition range with different compositions are also possible. Mixture with other glass powders is also possible, in order to combine specified effects.

Depending on the application area, components such as fluoride can be added to the glass up to concentrations of in total 5 percent by weight. This embodiment finds application in particular in the field of dental care/dental hygiene, since along with the antimicrobial and anti-inflammatory effect fluoride in low concentrations can be released through this embodiment, which hardens the dental enamel.

An especially preferred application in the dental area is the use of the described glasses for dental materials. In particular the inventive glasses are suitable either alone or in combination with other materials for tooth fillings, crowns, inlets. The use of the inventive glasses or glass ceramics and the glass powders or glass ceramic powders obtained from said inventive glasses or glass ceramics is especially preferred as composite material with polymer materials.

Without limiting the use of the described glasses in the polymer range, there are polymers that are especially well suited to the addition of bioglass. This are in particular PMMA; PVC; PTFE; PEEK; polystyrene; polyacrylate; polyethylene; polyester; polycarbonate; PGA biodegradable polymer; LGA biodegradable polymer or the biopolymer collages; fibrin; chitin; chitosan; polyamide; polycarbonate; polyester; polyimide; polyurea; polyurethane; organic fluorocarbon polymers; polyacrylamide and polyacrylic acids; polyacrylates; polymethacrylate; polyolefin; polystyrene and styrene co-polymers; poly vinyl ester; poly vinyl ether; poly vinylidene chloride; vinyl polymers; poly oxymethylene; poly aziridine; polyoxyalkylene; synthetic resin or alkyl resin, amino resin, epoxy resin, phenolic resin or unsaturated polyester resin; electric conducting polymers; high temperature polymers; inorganic polymers; poly phenylene oxide silicone; biopolymers such as cellulose, cellulose ester, cellulose ether, enzyme, gelatin, natural resin, nucleic acids, polysaccharide, proteins, silk, starch or wool.

Preferably the inventive glass possess a slight alkali content or are alkali-free in a preferred embodiment for use with alkali-sensitive polymers, such as e.g. polycarbonates.

In particular they are suitable for use in the following products, for example as an antimicrobial additive in polymers:

Cutting boards
Gloves
Garbage cans
Knife handles
Silverware, for example chopsticks
Trays
Table covers
Fibers for textiles
Refrigerators
Rinsing machines
Tumble dryers
Washing machines
Telephones
Keyboards
Irons Rice cookers
Steering wheels
Automobile instruments
Armrests
Keys
Door handles
Ash trays
Gear shift handle grips
Switches
Ballpoint pens
Diskettes
Audio/Video cassettes
Compact disks (CD)
Clipboards In addition such glasses, glass ceramics, glass powders or also glass ceramic powders can also find application in the area of the clothing industry, preferably as an additive to synthetic fibers.

A use in:
Clothing
Socks
Underwear
Hand towels
Toilet cloths
Wallpaper
Pillowcases
Pillow stuffing
Swim wear
Bathing caps
is conceivable.

Additional products based on synthetic fiber or polymer which can contain the inventive glass, the inventive glass ceramic, a glass powder or glass ceramic powder obtained from said inventive glass or glass ceramic are:
Carpeting
Contact lens
Contact lens holders
Play sand
Plastic money
Paper money
Toys
Wristwatches
Diving gear The antimicrobial glass powder as an admixture to the fibers is especially suitable in particular for use in fibers for carpeting.

The glass described in this invention or the glass ceramics or the glass powder or the glass powder ceramic obtained from said glass, which is obtained by means of grinding, is water soluble, but possesses sufficient chemical stability. The glass or glass powder acts first and foremost by means of ion exchange or ion transfer, which is connected with a surface reaction, and metal ion release.

Surprisingly the glass powders or glass ceramic powders in accordance with the invention evince a high reactivity and a higher antimicrobial effect than the group of bioactive glasses which were described in the state of the art or glass powders that were manufactured from such glasses.

In the following the invention will be described with the help of the embodiments.

First alkaline glass compositions with antimicrobial effect are described. The glasses are melted from the raw materials in a platinum crucible, and then processed into ribbons. The ribbons were further processed into powder with a particle size d50=4 μm by means of dry grinding.

In Table 1 the compositions and properties of glasses are given which can be grounded into the inventive glass powders and which exhibit an antimicrobial effect. The compositions refer to synthetic values in percent by weight on an oxide base.

Table 1: Compositions (synthetic values) [percent by weight] of Inventive glass compositions containing alkalis:

TABLE 1

Compositions (synthetic values) [percent by weight] of Inventive glass compositions containing alkalis:

|  | Embod. 1 | Embod. 2 | Embod. 3 | Embod. 4 | Embod. 5 | Embod. 6 | Embod. 7 |
|---|---|---|---|---|---|---|---|
| $P_2O_5$ | 66.1 | 70 | 68 | 66.1 | 67 | 75 | 67.5 |
| $SO_3$ | | | | | | | |
| $B_2O_3$ | | | | | | | |
| $Al_2O_3$ | 6.9 | 7 | 6.5 | 6.9 | 7 | 7 | 7 |
| $SiO_2$ | | | | | | | |
| $Li_2O$ | | | | | | | |
| $Na_2O$ | 10 | 10.5 | 9 | 10 | 12.2 | 9.0 | 11 |
| $K_2O$ | | | | | | | |
| CaO | | | 8 | | 13 | | |
| MgO | | | | | | | |
| SrO | | | | | | | |
| BaO | | | | | | | |
| ZnO | 16 | 12 | 8.5 | 10 | | 10 | 13.5 |
| $Ag_2O$ | 0.01 | 0.5 | | 0.5 | 0.8 | 2.0 | 1 |
| CuO | | | | | 0.01 | | |
| $GeO_2$ | | | | | | | |
| $TeO_2$ | | | | | | | |
| $Cr_2O_3$ | | | | | | | |
| I | | | | | | | |

The following Table 2 shows pH values and conductivities of glass powders of the composition as in Embodiments 1 and 2 as per Table in a 1 percent by weight aqueous suspension after 60 min.:

TABLE 2

|  | Embod. 1 | Embod. 2 | Embod. 3 | Embod. 4 | Embod. 5 | Embod. 6 |
|---|---|---|---|---|---|---|
| pH value | 5.5 | 5.1 | 6.9 | | 7.0 | |
| Conductivity (μS/cm) | 123 | — | 104 | | 1154 | |

In Table 3 the antimicrobial effect for Embodiment 2 as per Table 1 is given. 0.001 percent by weight of glass powder with a particle size of d50=4 μm of Embodiment 2 were measured in an aqueous suspension. The value 0 indicates that compared to the initial start value of for example 260,000 *E. coli* bacteria no more bacteria are present in the suspension, thus the antimicrobial effect of the glass powder had killed all colony-forming units.

TABLE 3

Antibacterial effect of the powders according to Europ. Pharmakopoe (3rd Edition) in 0.001 percent by weight of aqueous suspension: Embodiment 2 Particle size 4 μm:

|  | *E. coli* | *P. aeruginosa* | *S. aureus* | *C. albicana* | *A. niger* |
|---|---|---|---|---|---|
| Start | 260,000 | 350,000 | 280,000 | 360,000 | 280,000 |
| 2 days | 0 | 0 | 0 | 0 | 0 |
| 7 days | 0 | 0 | 0 | 0 | 0 |
| 14 days | 0 | 0 | 0 | 0 | 0 |
| 21 days | 0 | 0 | 0 | 0 | 0 |
| 28 days | 0 | 0 | 0 | 0 | 0 |

For a glass powder with a of d50=4 µm of the glass composition in accordance with Embodiment 2 in Table 1 a pH value of 5.1 was determined in a 1 percent by weight aqueous solution.

In particular the glass composition in accordance with Embodiment 3 in Table 2 represents a particularly preferable form, because it shows a pH-neutral value, combined with an antimicrobial and anti-inflammatory effect as well as special compatibility with body tissue.

Subsequently the antimicrobial effectiveness of different alkaline glass powders with a particle size of d50 of 4 µm and a glass composition in accordance with Embodiments 1, 2, 7 in Table 1 is described in a proliferation test.

A proliferation test is a test method with whose help the effectiveness of antimicrobial surfaces can be quantified. In the process, simply put, the antimicrobial effectiveness of the surface is characterized as to whether and how many daughter cells are transferred to a surrounding nutrient medium. The performance of the test is described in T. Bechert, P. Steinrücke, G. Guggenbichler, Nature Medicine, Volume 6, Number 8, September 2000, Pages 1053-1056.

The glass powder was homogenously introduced into different polymers. The polymers used were polypropylene (PP), acrylonitrile butadiene styrene (ABS) and polyamide PA.

Since the used glasses set a neutral to acid pH value, chain scissions which are normally induced by the presence of alkalis were able to be extensively suppressed here in the polymer.

*Staphylococcus epidermidis* was used as the germ. This germ is a bacterium which occurs on the skin.

In Table 4 the observed proliferation over a 48 hour period is shown for a glass powder with a particle size between d50 of 4 µm and a glass composition in accordance with Embodiment 1 in Table 1, which was homogenously introduced in the respective specified concentrations (percent by weight) into polypropylene (PP). By Onset OD the optical density in the surrounding nutrient medium is meant. By means of proliferation (formation of daughter cells) and transfer of the cells from the surface to the surrounding nutrient medium an impairment of the transmission of the nutrient medium takes place. This absorption with specified wavelengths correlates with the antimicrobial effectiveness of the surface. The higher the Onset OD value, the more strongly antimicrobially effective the surface is. This definition of the size OD also refers to the all the subsequent tables.

TABLE 4

Glass powder of a glass composition
in accordance with Embodiment 1:
Polymer used: Polypropylene (PP)

|  | Glass powder amount in percent by weight | |
| --- | --- | --- |
|  | 0.10% | 1.00% |
| Onset OD (absolute) | 5.7 | 15.7 |
| Assessment | Very slightly antibacterial | Antibacterial |

In Table 5 the observed proliferation over 48 hours is shown for a glass powder with a particle size between d50 of 4 m and a glass composition in accordance with Embodiment 7 in Table 1, which was homogenously introduced in the respective specified concentrations (percent by weight) into polypropylene (PP).

TABLE 5

Glass powder of a glass composition
in accordance with Embodiment 7:
Polymer used: Polypropylene (PP)

|  | Glass powder amount in percent by weight | | | |
| --- | --- | --- | --- | --- |
|  | 0.20% | 0.50% | 2.00% | 5.00% |
| Onset OD (absolute) | 8.1 | 11.6 | 18.5 | 30.1 |
| Assessment | mild anti-bacterial activity | slightly anti-bacterial | anti-bacterial | highly anti-bacterial |

In Table 6 the observed proliferation over 48 hours is shown for a glass powder with a particle size between d50 and 4 µm and a glass composition in accordance with Embodiment 1 in Table 1, which was homogenously introduced in the respective specified concentrations (percent by weight) into acrylonitrile butadiene styrene (ABS).

TABLE 6

Glass powder of a glass composition
in accordance with Embodiment 1:
Polymer used: acrylonitrile butadiene styrene (ABS)

|  | Glass powder amount in percent by weight | |
| --- | --- | --- |
|  | 0.10% | 1.00% |
| Onset OD (absolute) | 7.7 | 16.7 |
| Assessment | Mild antibacterial activity | Antibacterial |

In Table 7 the observed proliferation over 48 hours is shown for a glass powder with a particle size between d50 and 4 µm and a glass composition in accordance with Embodiment 2 in Table 1, which was homogenously introduced in the respective specified concentrations (percent by weight) into acrylonitrile butadiene styrene (ABS).

TABLE 7

Glass powder of a glass composition
in accordance with Embodiment 2:
Polymer used: acrylonitrile butadiene styrene (ABS)

|  | Glass powder amount in percent by weight | |
| --- | --- | --- |
|  | 0.10% | 1.00% |
| Onset OD (absolute) | 7.5 | 19.6 |
| Assessment | Mild antibacterial activity | Antibacterial |

In Table 8 the observed proliferation over 48 hours is shown for a glass powder with a particle size between d50 and 4 µm and a glass composition in accordance with Embodiment 1 in Table 1, which was homogenously introduced in the respective specified concentrations (percent by weight) into polyamide (PA).

TABLE 8

Glass powder of a glass composition
in accordance with Embodiment 2:
Polymer used: polyamide (PA)

| | Glass powder amount in percent by weight | |
|---|---|---|
| | 0.10% | 1.00% |
| Onset OD (absolute) | 6 | 10.9 |
| Assessment | Very slightly antibacterial | Slightly Antibacterial |

In Table 9 the observed proliferation over 48 hours is shown for a glass powder with a particle size between d50 and 4 μm and a glass composition in accordance with Embodiment 2 in Table 1, which was homogenously introduced in the respective specified concentrations (percent by weight) into polyamide (PA).

TABLE 9

Glass powder of a glass composition
in accordance with Embodiment 2:
Polymer used: polyamide (PA)

| | Glass powder amount in percent by weight | |
|---|---|---|
| | 0.10% | 1.00% |
| Onset OD (absolute) | 7.2 | 32.4 |
| Assessment | Mild antibacterial activity | antimicrobial |

In the following the invention relative to alkali-free glasses will be described with the help of the embodiments.

In addition to the conventional melting process the described alkali-free glasses can also be manufactured via the sol-gel method.

The alkali-free glasses were melted from the raw materials in a platinum crucible, and then processed into ribbons. The ribbons were further processed into powder with a particle size d50=4 μm by means of dry grinding.

In Table 1 the compositions and properties of alkali-free glasses are given which can be grounded into the inventive glass powders. The compositions refer to synthetic values in percent by weight on an oxide base.

In Table 11 the antimicrobial effect for Embodiment 1 in accordance with Table 10 is given. 0.001 percent by weight of glass powder with a particle size of d50=4 μm of Embodiment 1 was measured in an aqueous suspension.

TABLE 11

Antibacterial effect of the powders according to Europ. Pharmakopoe
(3rd Edition) in 0.001 percent by weight of aqueous suspension:
Embodiment 1 as per Table 9; Particle size 4 μm:

| | E. coli | P. aeruginosa | S. aureus | C. albicana | A. niger |
|---|---|---|---|---|---|
| Start | 240,000 | 340,000 | 240,000 | 330,000 | 280,000 |
| 2 days | 0 | 0 | 0 | 55,000 | 220,000 |
| 7 days | 0 | 0 | 0 | 40,000 | 200,000 |
| 14 days | 0 | 0 | 0 | 0 | 0 |
| 21 days | 0 | 0 | 0 | 0 | 0 |
| 28 days | 0 | 0 | 0 | 0 | 0 |

Table 12 specifies the antimicrobial effect for Embodiment 2 as per Table 10. 0.01 percent by weight of glass powder with a particle size of d50=4 μm of Embodiment 2 was measured in an aqueous suspension.

TABLE 12

Antibacterial effect of the powders according to Europ. Pharmakopoe
(3rd Edition) in 0.01 percent by weight of aqueous suspension:
Embodiment 2 as per Table 9: Particle size 4 μm:

| | E. coli | P. aeruginosa | S. aureus | C. albicana | A. niger |
|---|---|---|---|---|---|
| Start | 240,000 | 340,000 | 240,000 | 330,000 | 280,000 |
| 2 days | 0 | 100 | 100 | 32,000 | 260,000 |
| 7 days | 0 | 0 | 0 | 12,000 | 240,000 |
| 14 days | 0 | 0 | 0 | 4,400 | 200,000 |
| 21 days | 0 | 0 | 0 | 1,000 | 140,000 |
| 28 days | 0 | 0 | 0 | 1,000 | 140,000 |

Subsequently the antimicrobial effectiveness of a glass powder with a particle size of d50 of 4 μm and a glass composition in accordance with Embodiment 1 in Table 10 is described in a proliferation test.

A proliferation test is a test method with whose help the effectiveness of antimicrobial surfaces can be quantified. In the process, simply put, the antimicrobial effectiveness of the

TABLE 10

Compositions (synthetic values) [percent by weight] of
Inventive alkali-free glass compositions

| | Embod. 1 | Embod. 2 | Embod. 3 | Embod. 4 | Embod. 5 | Embod. 6 | Embod. 7 | Embod. 8 | Embod. 9 |
|---|---|---|---|---|---|---|---|---|---|
| $P_2O_5$ | 65.9 | 65.9 | 75 | 67 | 72 | 67 | 70 | 80 | 70 |
| $SO_3$ | | | | | | | | | |
| $B_2O_3$ | | | 1 | | | | | | |
| $Al_2O_3$ | 6.2 | 6.2 | 0 | 0 | 5 | 5 | 4 | 3 | 3 |
| $SiO_2$ | | | | | | | | | |
| CaO | 11.9 | 11.9 | 13 | 11 | 20 | 8 | 5 | 5 | |
| MgO | | | 8.5 | | | | | | 5 |
| SrO | | | | | | | | 2.7 | |
| BaO | | | | | | | 5 | | |
| ZnO | 15 | 16 | 2 | 22 | 2 | 20 | 15 | 9 | 21.2 |
| $Ag_2O$ | 1 | | 0.5 | | 1 | | 0.5 | | |
| CuO | | | | | | | | | 0.5 |
| $GeO_2$ | | | | | | | | | 0.2 |
| $TeO_2$ | | | | | | | 0.5 | | |
| $Cr_2O_3$ | | | | | | | | | 0.1 |
| I | | | | | | | | 0.3 | | surface is characterized as to whether and how many daughter cells are transferred to a surrounding nutrient medium. The performance of the test is described in T. Bechert, P. Steinrücke, G. Guggenbichler, Nature Medicine, Volume 6, Number 8, September 2000, Pages 1053-1056.

The glass powder was homogenously introduced into a polymer.

*Staphylococcus epidermidis* was used as the germ. This germ is a bacterium which occurs on the skin.

In Table 13-14 the observed proliferation over a 48 hour period is shown for a glass powder with a particle size between d50 of 4 µm and a glass composition in accordance with Embodiment 1, which was homogenously introduced in the respective specified concentrations (percent by weight) into acrylonitrile butadiene styrene (ABS) and polystyrene (PS). By Onset OD the optical density in the surrounding nutrient medium is meant. By means of proliferation (formation of daughter cells) and transfer of the cells from the surface to the surrounding nutrient medium an impairment of the transmission of the nutrient medium takes place. This absorption with specified wavelengths correlates with the antimicrobial effectiveness of the surface. The higher the Onset OD value, the more strongly antimicrobially effective the surface is.

TABLE 13

| Embodiment 1: Polymer used: ABS (acrylonitrile butadiene styrene) | | |
|---|---|---|
| | 0.50% | 2.00% |
| Onset OD (absolute) | 11.6 | 20.8 |
| Assessment | No activity | Antimicrobial |

TABLE 14

| | 0.50% | 2.00% |
|---|---|---|
| Embodiment 1: Polymer used: PS (polystyrene) | | |
| Onset OD (absolute) | 22.1 | Limit |
| Assessment | No activity | bactericide |
| Embodiment 2: Polymer used: PS (polystyrene) | | |
| Onset OD (absolute) | 8 | 11.4 |
| Assessment | No activity | Slightly antimicrobial |

With the inventive phosphate glass composition for the first time a glass composition is specified which exhibits an antimicrobial long-term effect. In particular glass powders or glass ceramic powders of such a glass composition also evince an antimicrobial effect when they are included in a polymer matrix.

In addition a polymer-glass-composite is specified which comprises such a glass composition and stands out due to a high antimicrobial effect as well as due to a high resistance. Such polymer-glass-composite materials are especially preferably manufactured by mixing a polymer with a glass powder yielding a polymer-glass powder mixture. This polymer glass powder mixture is then subjected to a heat treatment in a mixer, for example by means of heating the glass powder mixture to a temperature in the range of +50° C. to +350° C. under thorough mechanical mixing. A plastic-glass-composite-material then develops in which the glass can partially melt and an intimate combination of the glasses with a particularly high melting polymer occurs, which results in an extremely homogenous distribution of the glass in the polymer.

The obtained plastic-glass-composite-material can be further processed by grinding e.g. into a pellet or directly into a plastic semi-finished product or plastic end product, for example by means of injection molding.

The invention claimed is:

1. Antimicrobial acting phosphate glass or glass ceramic in the form of a water-soluble powder, comprising the following composition in percent by weight on an oxide basis

| | | |
|---|---|---|
| $P_2O_5$ | >66-80 | percent by weight |
| $SO_3$ | 0-16.8 | percent by weight |
| $B_2O_3$ | 0-1 | percent by weight |
| $Al_2O_3$ | >6.2-10 | percent by weight |
| $SiO_2$ | 0-10 | percent by weight |
| $Na_2O$ | >11.0-20 | percent by weight |
| $Li_2O$ | 0 | percent by weight |
| $K_2O$ | 0 | percent by weight |
| CaO | 0-16.8 | percent by weight |
| MgO | 0-15 | percent by weight |
| SrO | 0-15 | percent by weight |
| BaO | 0-15 | percent by weight |
| ZnO | >0-16.8 | percent by weight |
| $Ag_2O$ | 0-5 | percent by weight |
| CuO | 0-10 | percent by weight |
| $GeO_2$ | 0-10 | percent by weight |
| TeO2 | 0-15 | percent by weight |
| $Cr_2O_3$ | 0-10 | percent by weight |
| I | 0-10 | percent by weight |
| F | 0-3 | percent by weight. |

2. Antimicrobial acting phosphate glass or glass ceramic in accordance with claim 1, characterized by the fact that the composition comprises less than 0.01 percent by weight $B_2O_3$, preferably being free from B except for impurities.

3. Antimicrobial acting phosphate glass or glass ceramic in accordance with claim 1, characterized by the fact that the composition comprises 5-16.8 percent by weight CaO.

4. Antimicrobial acting phosphate glass or glass ceramic in accordance with claim 1, characterized by the fact that the composition comprises 5-16.8 percent by weight ZnO.

5. Antimicrobial acting phosphate glass or glass ceramic in accordance with claim 1, characterized by the fact that the composition comprises >12- 16.8 percent by weight ZnO.

6. Anticrobial acting phosphate glass or glass ceramic in accordance with claim 1, characterized by the fact that the composition comprises 0-<1.2 percent by weight $Ag_2O$.

7. Antimicrobial acting phosphate glass or glass ceramic in accordance with claim 1, characterized by the fact that the sum $Ag_2O$ +CuO +$GeO_2$+$TeO_2$+$Cr_2O_3$+I+F+ZnO amounts to between 0.01 and 16.8 percent by weight.

8. Antimicrobial acting phosphate glass or glass ceramic in accordance with claim 1, characterized by the fact that the sum ZnO+CaO+MgO ranges between 10 and 16.8 percent by weight.

9. Antimicrobial acting phosphate glass or glass ceramic in accordance with claim 1, characterized by the fact that the composition comprises 67-76 percent by weight $P_2O_5$.

10. Antimicrobial acting glass or glass ceramic in accordance with claim 1, said powder having an average particle size of <20 µm.

11. Antimicrobial acting glass or glass ceramic in accordance with claim 1, said powder having an average particle size of <10 µm.

12. Antimicrobial acting glass or glass ceramic in accordance with claim 1, said powder having an average particle size of <5 µm.

13. Antimicrobial acting glass or glass ceramic in accordance with claim 1, said powder having an average particle size of <1 µm.

14. Antimicrobial acting glass or glass ceramic comprising the glass composition of claim 1, for use in cosmetic products.

15. Antimicrobial acting glass or glass ceramic comprising the glass composition of claim 1, for use in deodorant products.

16. Antimicrobial acting glass or glass ceramic comprising the glass composition of claim 1, for use in medical products and preparations.

17. Antimicrobial acting glass or glass ceramic comprising the glass composition of claim 1, for use in plastics and polymers.

18. Antimicrobial acting glass or glass ceramic comprising the glass composition of claim 1, for use in the field of paper hygiene.

19. Antimicrobial acting glass or glass ceramic comprising the glass composition of claim 1, for use in food.

20. Antimicrobial acting glass or glass ceramic comprising the glass composition of claim 1, for use in detergents.

21. Antimicrobial acting glass or glass ceramic comprising the glass composition of claim 1, for use in paints and lacquers.

22. Antimicrobial acting glass or glass ceramic comprising the glass composition of claim 1, for use in plasters, cements and concrete.

23. Antimicrobial acting glass or glass ceramic comprising the glass composition of claim 1, for use in products of oral hygiene, dental care, oral care, palatine hygiene, palatine care.

24. Antimicrobial acting phosphate glass or glass ceramic in accordance with claim 1, said composition having a ratio of Na/Al of between 2:1 and 1:1.

25. Antimicrobial acting phosphate glass ceramic, characterized by the fact that the glass ceramic is obtained from a source glass with a glass composition in accordance with claim 1.

26. Antimicrobial acting glass or glass ceramic powder comprising the glass ceramic of claim 25.

* * * * *